(12) United States Patent
Lee et al.

(10) Patent No.: US 10,791,269 B2
(45) Date of Patent: Sep. 29, 2020

(54) OPERATION METHOD AND SYSTEM FOR CAMERA OPERATION APPARATUS, AND APPARATUS THEREFOR

(71) Applicant: Hanwha Techwin Co., Ltd., Changwon-si (KR)

(72) Inventors: Min Gyu Lee, Changwon-si (KR); Mee Jee Jeong, Changwon-si (KR); Il Hwang Cha, Changwon-si (KR); Hyun Gyu Lee, Changwon-si (KR)

(73) Assignee: HANWHA TECHWIN CO., LTD., Seongnam-si (KR)

( * ) Notice: Subject to any disclaimer, the term of this patent is extended or adjusted under 35 U.S.C. 154(b) by 0 days.

(21) Appl. No.: 15/945,264

(22) Filed: Apr. 4, 2018

(65) Prior Publication Data

US 2018/0227491 A1    Aug. 9, 2018

Related U.S. Application Data

(63) Continuation of application No. PCT/KR2016/009290, filed on Aug. 23, 2016.

(30) Foreign Application Priority Data

Feb. 5, 2016   (KR) .................. 10-2016-0014722

(51) Int. Cl.
*H04N 5/232* (2006.01)
*A61B 5/00* (2006.01)
(Continued)

(52) U.S. Cl.
CPC ....... *H04N 5/23245* (2013.01); *A61B 5/0402* (2013.01); *A61B 5/746* (2013.01);
(Continued)

(58) Field of Classification Search
CPC ......... A61B 5/00; A61B 5/1486; A61B 5/145; H03M 7/6047; H03M 7/3062; H03M 7/6058
(Continued)

(56) References Cited

U.S. PATENT DOCUMENTS

2015/0351641 A1    12/2015 Kang et al.
2016/0367138 A1*   12/2016 Kim ..................... A61B 5/6803
(Continued)

FOREIGN PATENT DOCUMENTS

EP            2698686 A2    2/2014
KR    10-2009-0107414 A    10/2009
(Continued)

OTHER PUBLICATIONS

International Search Report, issued by International Searching Authority in corresponding International Application No. PCT/KR2016/009290, dated Nov. 29, 2016, (PCT/ISA/210).
(Continued)

*Primary Examiner* — Christopher Braniff
(74) *Attorney, Agent, or Firm* — Sughrue Mion, PLLC (57) ABSTRACT

Provided are an operation method for a camera operation apparatus, the method including the steps of: obtaining a bio-signal of a user from a wearable sensor; determining, based on the bio-signal, whether a state of a user is a stable state; setting the camera to a low power mode if the state of the user is a stable state; determining the type of bio-signal if the state of the user is not a stable state; and setting the camera to a mode in accordance with the type of the bio-signal.

16 Claims, 9 Drawing Sheets

(51) Int. Cl.
    *G08B 13/196*     (2006.01)
    *G08B 25/08*     (2006.01)
    *A61B 5/0402*     (2006.01)
    *G08B 21/04*     (2006.01)
    *A61B 5/01*     (2006.01)
    *A61B 5/0488*     (2006.01)
    *A61B 5/0476*     (2006.01)

(52) U.S. Cl.
    CPC ... *G08B 13/19602* (2013.01); *G08B 21/0453* (2013.01); *G08B 25/08* (2013.01); *H04N 5/23219* (2013.01); *H04N 5/23222* (2013.01); *H04N 5/232411* (2018.08); *A61B 5/0022* (2013.01); *A61B 5/0077* (2013.01); *A61B 5/01* (2013.01); *A61B 5/0476* (2013.01); *A61B 5/0488* (2013.01); *A61B 2560/0209* (2013.01)

(58) Field of Classification Search
    USPC .......................................... 348/77, 143–161
    See application file for complete search history.

(56) References Cited

U.S. PATENT DOCUMENTS

2017/0215753 A1    8/2017    Lee
2019/0036545 A1*    1/2019    Natarajan ............... H03M 7/30

FOREIGN PATENT DOCUMENTS

| KR | 10-2010-0099881 A | 9/2010 |
|----|-------------------|--------|
| KR | 10-2011-0005927 A | 1/2011 |
| KR | 10-1465587 B1 | 11/2014 |
| KR | 10-1489896 B1 | 2/2015 |
| KR | 10-2015-0109993 A | 10/2015 |
| KR | 10-1569880 B1 | 11/2015 |

OTHER PUBLICATIONS

Written Opinion, issued by International Searching Authority in corresponding International Application No. PCT/KR2016/009290, dated Nov. 29, 2016, (PCT/ISA/237).

* cited by examiner

| KIND OF BIO-SIGNAL | ECG SENSOR | TEMP SENSOR | TYPE OF BIO-SIGNAL | CAMERA MODE | ADDITIONAL OPERATION |
|---|---|---|---|---|---|
| ECG + TEMP | DETECT RAPID DECREASE | TEMPERATURE DROP (COMPARED WITH REFERENCE) | HEART ATTACK, RISK OF CARDIAC ARREST | – REAL-TIME LIVE MODE | – SEND ALARM TO USER AND CONTROL CENTER<br>– CALL PARAMEDICS<br>– TRANSMIT REAL-TIME IMAGES AND LOCATION<br>– REPRODUCE FIRST-AID TREATMENT |
| | INCREASED STATE CONTINUES | TEMPERATURE RISE (COMPARED WITH REFERENCE) | BRISK WALKING, RUNNING | – ACTION CAM MODE | – INCREASE FRAME RATE<br>– TURN IMAGE STABILIZER ON |
| | INCREASE SMALL AMOUNT (COMPARED WITH REFERENCE) | TEMPERATURE RISE (COMPARED WITH REFERENCE) | EXCITEMENT AND JOY | – HIGH-RESOLUTION IMAGING MODE | – EXECUTE RECORDING FUNCTION |
| | MAINTAIN CONSTANT LEVEL | CONSTANT TEMPERATURE | RELAXED STATE | – LOW-POWER MODE | – DECREASE FRAME RATE<br>– TURN IMAGE STABILIZER OFF |
| | DECREASE SMALL AMOUNT (COMPARED WITH REFERENCE) | TEMPERATURE DROP (COMPARED WITH REFERENCE) | DEPRESSED STATE | – REAL-TIME LIVE MODE | – SEND ALERT TO FAMILY OR FRIEND<br>– TRANSMIT REAL-TIME IMAGES AND LOCATION |

OPERATION METHOD AND SYSTEM FOR CAMERA OPERATION APPARATUS, AND APPARATUS THEREFOR

CROSS-REFERENCE TO THE RELATED APPLICATION

This Application is a continuation application of PCT Application No. PCT/KR2016/009290 filed on Aug. 23, 2016, which claims priority from Korean Patent Application No. 10-2016-0014722 filed on Feb. 5, 2016, the disclosure of which is incorporated herein by reference.

TECHNICAL FIELD

The present disclosure relates to a method and system for operating a camera operating apparatus and an apparatus therefor, and more particularly, to a method and system for a camera operating apparatus capable of changing an operating mode of a camera based on bio-signals of a user collected by a wearable sensor, and an apparatus therefor.

BACKGROUND ART

A user who uses a camera has to change a frame rate and a resolution of the camera to an appropriate operation mode according to the situation of the user. When the user is in an emergency situation, an appropriate image may not be obtained according to the situation because it may not be possible to change the operating mode of the camera.

DESCRIPTION OF EMBODIMENTS

Technical Problem

Provided are a method and system for operating a camera based on bio-signals, for automatically changing an operating mode of the camera based on bio-signals of a user obtained from a wearable sensor, and an apparatus therefor.

Solution to Problem

According to an aspect of the present disclosure, a method of operating a camera operating apparatus, the method includes: obtaining a bio-signal of a user from a wearable sensor; determining, based on the bio-signal, whether the user is in a stable state; when the user is in the stable state, setting a camera to a low-power mode; when the user is not in the stable state, determining a type of the bio-signal; and setting the camera to a mode according to the type of the bio-signal.

The determining of whether the user is in the stable state may include, when a value measured by an electrocardiogram (ECG) sensor in the wearable sensor is within a reference ECG range set in advance and a value measured by a temperature sensor in the wearable sensor is within a reference temperature range set in advance, determining that the user is in stable state.

The setting of the low-power mode may include setting a frame rate of the camera to be equal to or less than a reference frame rate set in advance, and turning off an image stabilizing function of the camera.

The camera may be a wearable camera provided on a body of the user, or may be provided in an external environment.

The method may further include setting a communication connection to the camera.

The method may further include, when the camera is set to one of a real-time live mode, an action cam mode, and a high-resolution imaging mode in the setting of the mode, storing every frame included in images transmitted from the camera, within a time range corresponding to a time point when it is determined that the user is not in the stable state.

The method may further include storing every frame after mapping the bio-signal to each frame, within the time range corresponding to the time point when it is determined that the user is not in the stable state.

The method may further include, when the camera is set to the low-power mode in the setting of the mode, storing, according to a frame selecting condition set in advance, only some of a plurality of frames included in images transmitted from the camera.

The method may further include transmitting a feedback signal to the wearable sensor, based on an operation result of the camera.

According to an aspect of the present disclosure, a camera operating apparatus includes: a bio-signal obtainer configured to obtain a bio-signal of a user from a wearable sensor; a user condition determiner configured to determine, based on the bio-signal, whether the user is in a stable state; a bio-signal type determiner configured to determine a type of the bio-signal, when the user is not in the stable state; and a camera mode setting unit configured to set the camera to a low-power mode when the user is in the stable state, and set the camera to a mode according to a type of the bio-signal when the user is not in the stable state.

The wearable sensor may include an electroencephalography (EEG) sensor, an electromyography (EMG) sensor, an electrocardiogram (ECG) sensor, and a temperature sensor.

The camera operating apparatus may further include a feedback signal transmitter configured to transmit a feedback signal to the wearable sensor based on an operating result of the camera.

The camera may be a wearable camera provided on a body of the user, or may be provided in an external environment.

The camera operating apparatus may further include a communication connection unit configured to establish a communication connection to the camera.

According to an aspect of the present disclosure, a camera operating system includes: at least one wearable sensor configured to obtain a bio-signal of a user; a camera configured to capture images; and a camera operating apparatus configured to obtain the bio-signal, to determine a condition of the user based on the bio-signal, and to set a mode of the camera based on the condition of the user.

Other aspects, features and advantages of the present disclosure will become better understood through the accompanying drawings, the claims and the detailed description.

Advantageous Effects of Disclosure

According to a method and system for operating a camera based on bio-signals and an apparatus therefor of the present disclosure, an operating mode of the camera may be automatically changed based on bio-signals of a user obtained by a wearable sensor.

Also, according to embodiments of the present disclosure, an operating mode of the camera is changed according to bio-signals of a user, and thus, images may be obtained according to situations and a memory may be used more efficiently.

According to embodiments of the present disclosure, a user's condition may be easily checked from each time point in an image.

BEST MODE

As the present disclosure allows for various changes and numerous embodiments, particular embodiments will be illustrated in the drawings and described in detail in the written description. However, this is not intended to limit the present disclosure to particular modes of practice, and it is to be appreciated that all modifications, equivalents, and/or alternatives that do not depart from the spirit and technical scope are encompassed in the disclosure. In the description, certain detailed explanations of the related art are omitted when it is deemed that they may unnecessarily obscure the essence of the present disclosure.

It will be understood that although the terms "first," "second," etc. may be used herein to describe various components, these components should not be limited by these terms. Terms are only used to distinguish one element from other elements.

The terms used in the present specification are merely used to describe particular embodiments, and are not intended to limit the present disclosure. An expression used in the singular encompasses the expression of the plural, unless it has a clearly different meaning in the context. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Some embodiments of the present disclosure may be represented as functional block structures and various processing stages. The functional blocks may be implemented as variety numbers hardware and/or software configurations executing certain functions. For example, the inventive concept may employ various integrated circuit (IC) components, e.g., memory elements, processing elements, logic elements, look-up tables, and the like, which may carry out a variety of functions under the control of one or more microprocessors or other control devices. Similarly, where the elements are implemented using software programming or software elements, the inventive concept may be implemented with any programming or scripting language such as C, C++, Java, assembler language, or the like, with the various algorithms being implemented with any combination of data structures, objects, processes, routines or other programming elements. The functional aspects may be implemented in algorithms that are executed on one or more processors. Also, the present disclosure may employ any number of conventional techniques for electronics configuration, signal processing and/or control, data processing and the like. The words "mechanism," "element," "means," and "configuration" are used broadly and are not limited to mechanical or physical embodiments. The above terms may include software routines in conjunction with processors, etc.

Also, in the present specification and drawings, like reference numerals denote substantially the same components and detailed descriptions thereof are not repeated.

Figure 1:
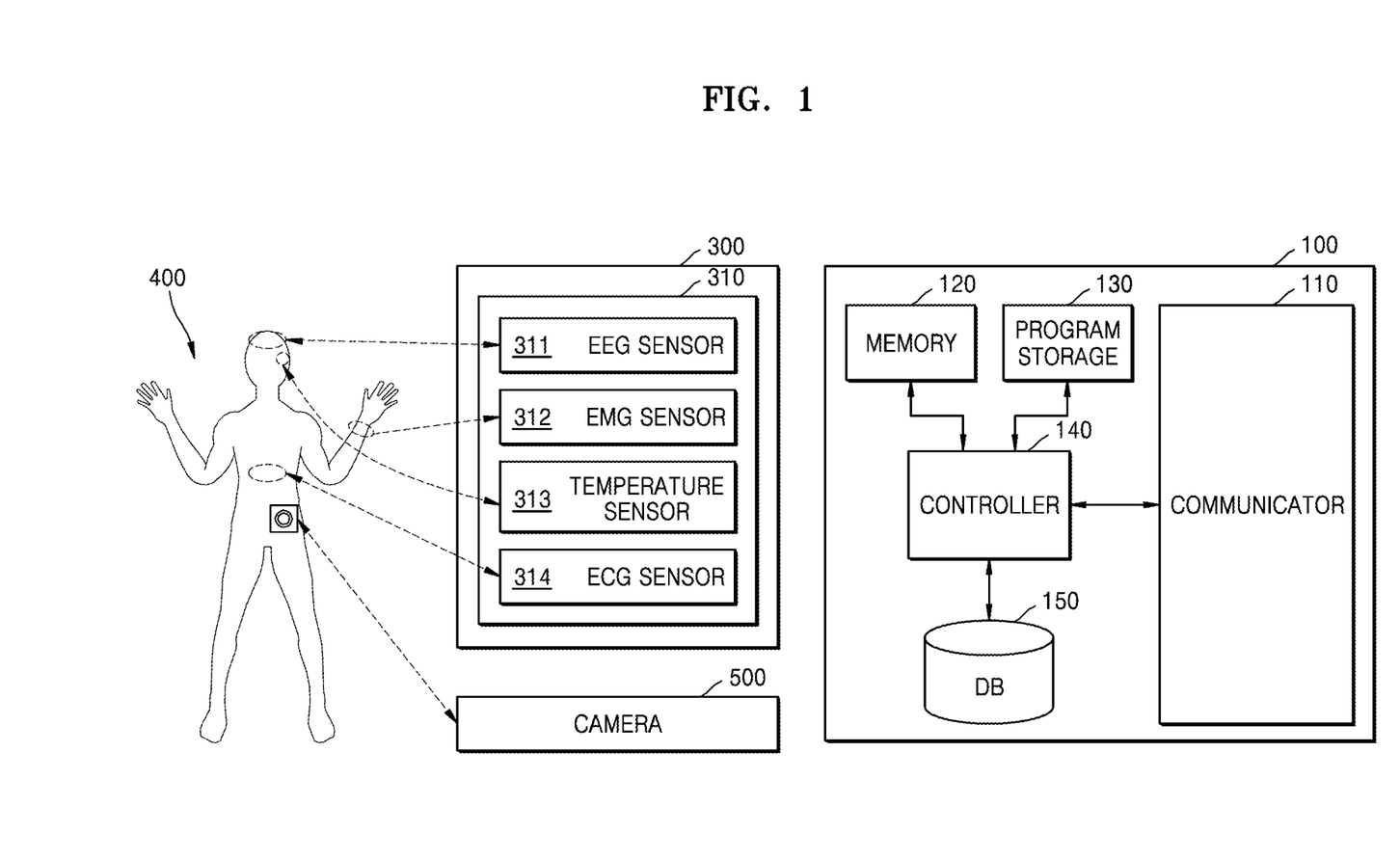
FIG. 1 is a block diagram of a camera operating system based on bio-signals, according to an embodiment of the present disclosure.

FIG. 1 is a block diagram of a camera operating system based on bio-signals, according to an embodiment of the present disclosure.

Referring to FIG. 1, a camera operating system based on a bio-signal, according to an embodiment of the present disclosure, may include a camera operating apparatus 100, a wearable device 300, and a camera 500.

The camera operating apparatus 100, the wearable device 300, and the camera 500 may be separately provided and connected to one another through wires or wirelessly, and the camera operating apparatus 100 may include at least one of the wearable device 300 and the camera 500.

In addition, the wearable device 300 may be provided in clothing or accessories that a user 400 may wear, and may be provided as an accessory itself directly worn on the user 400 such as a hair band, a wrist band, a waist belt, etc.

The camera operating apparatus 100 according to the embodiment of the present disclosure provides a driving signal to the camera 500 based on bio-signals of the user 400 transmitted from the wearable device 300.

The camera operating apparatus 100 may include a communicator 110, a memory 120, a program storage 130, a controller 140, and a database 150.

In detail, the communicator 110 provides a communication interface that is necessary to provide transmission/reception signals between the camera operating apparatus 100 and another terminal (not shown) or a server (not shown) in the form of packet data, in line with a communication network. Moreover, the communicator 110 may transmit a result of driving the wearable device 300 to a personal terminal (not shown) of the user 400 or a designated wearable device control server (not shown).

Here, the communicator 110 may be a device including hardware and software that are necessary for transmitting/receiving signals such as control signals or data signals to/from another network device through wired/wireless connection.

The communication network may include a wired network such as local area network (LAN), wide area network (WAN), metropolitan area network (MAN), integrated service digital network (ISDN), etc., or a wireless network such as wireless LAN, CDMA, Bluetooth, satellite communication, etc., but is not limited thereto.

The memory 120 may temporarily or permanently store data processed by the controller 140. Here, the memory 120 may include a magnetic storage medium or a flash storage medium, but is not limited thereto.

The program storage 130 has control software thereon for performing an operation of obtaining bio-signals, an operation of determining a user's condition, an operation of determining a type of the bio-signal, an operation of setting a camera mode, an operation of generating a feedback signal, etc.

The controller 140 is a kind of central processing device, and controls overall processes of operating the camera. That is, the controller 140 operates the control software loaded on the program storage 130 to obtain bio-signals of the user 400 from the wearable device 300, and determines a condition of the user 400, etc.

Here, the controller 140 may include all kinds of devices capable of processing data, such as a processor. Here, the 'processor' may denote a data processing device built in hardware, and includes a physically structured circuit for executing functions expressed as codes or commands included in a program.

Thus, as an example of the data processing device built into the hardware, a microprocessor, a central processing unit (CPU), a processor core, a multiprocessor, an application-specific integrated circuit (ASIC), a field programmable gate array (FPGA), etc., but the scope of the present disclosure is not limited thereto.

The database 150 includes information about standards for determining a stable state of a user according to the bio-signals of the user, information about standards for determining types of the bio-signals, etc. Also, the database 150 may store images transmitted from the camera 500. Images may be stored after being categorized according to types of the bio-signals.

In addition, the camera operating apparatus 100 may further include a display (not shown) for displaying images transmitted from the camera 500 and/or images stored in the database 150, displaying bio-signals, and displaying a setting interface of the camera operating apparatus 100.

For example, the display (not shown) may include, but is not limited thereto, one of a cathode ray tube (CRT), a liquid crystal display (LCD), a plasma display panel (PDP), and an organic light-emitting diode (OLED).

In addition, the display (not shown) may further include an input unit for obtaining a user input. For example, the display (not shown) may further include a digitizer that reads a coordinate of a point touched by the user and converts the coordinate into an electrical signal, in order to obtain the user input according to a screen displayed on the display. Therefore, the display (not shown) may be a touch screen including a touch panel. Here, the touch panel may further read a touch pressure as well as touch coordinates of the user and convert the touch pressure into an electrical signal.

An input unit may be separately provided from the display (not shown). For example, the input unit may include one of a keyboard, a mouse, a trackball, a microphone, and a button that are separately provided from the display (not shown).

Hereinafter, it will be assumed that the display (not shown) is a touch screen including an input unit capable of determining whether there is a touch operation of the user and determining the touch pressure, but the present disclosure is not limited thereto.

The wearable device 300 according to the embodiment of the present disclosure includes a wearable sensor 310. When the wearable sensor 310 obtains bio-signals of the user 400 and transmits the bio-signals to the camera operating apparatus 100, the camera operating apparatus 100 determines an operating mode of the camera 500 based on the received bio-signals, and the camera 500 receives a driving signal according to the determined operating mode, from the camera operating apparatus 100, and operates.

Each of the components of the camera operating apparatus 100, the wearable device 300, and the camera 500 may be a device that is physically separate from the others, or may be the same device and only conceptionally separated.

The wearable sensor 310 may include an electroencephalography (EEG) sensor 311, an electromyography (EMG) sensor 312, a temperature sensor 313, and an electrocardiogram (ECG) sensor 314.

The EEG sensor 311 may measure an electrical signal generated when signals are transmitted among cranial nerves of the user 400.

The EMG sensor 312 may measure electrical signals generated from skeletal muscles of the user 400.

The temperature sensor 313 may measure a body temperature of the user 400.

The ECG sensor 314 may measure electrical signals sensed from skin according to cardiac activity of the user 400.

However, the above-described wearable sensor 310 is an example and the present disclosure is not limited thereto, that is, any kind of unit may be used provided that the bio-signals of the user 400 may be sensed. For example, the wearable sensor 310 may further include blood pressure sensor and iris recognition sensor.

The camera 500 according to the embodiment of the present disclosure includes a lens and an image sensor, and may obtain images. As described above, the camera 500 may be included in one of the camera operating apparatus 100 and the wearable device 300, or may be separately provided. Moreover, when the camera 500 is separately provided from the camera operating apparatus 100 and the wearable device 300, the camera 500 may be provided on a body of the user 400 or may be provided in an external environment.

The camera 500 may be set to operate in one of various operating modes. For example, the camera 500 may be set to one of operating modes such as a real-time live mode, an action cam mode, a high-resolution imaging mode, and a low-power mode.

The real-time live mode is a mode for transmitting obtained images to the camera operating apparatus 100 in real time.

The action cam mode may be a mode of capturing images after setting a frame rate of the camera 500 to be equal to or greater than a reference frame rate and turning on an image stabilizing function.

The high-resolution imaging mode may be a mode of capturing images after setting a resolution of the camera 500 to be equal to or greater than a reference resolution.

The low-power mode may be a mode of capturing images after setting a frame rate of the camera 500 to be less than the reference frame rate and turning off the image stabilizing function.

When the camera 500 operates in each of the modes, the camera operating apparatus 100 may also operate in a mode corresponding to the operating mode of the camera 500.

For example, when the camera 500 operates in one of the real-time live mode, the action cam mode, and the high-resolution imaging mode, the camera operating apparatus 100 may operate in a black-box mode or a health-care mode. In addition, when the camera 500 operates in the low-power mode, the camera operating apparatus 100 may also operate in a low-power mode.

Here, the black-box mode of the camera operating apparatus 100 may be a mode for storing all frames included in the images transmitted from the camera 500, within a time range corresponding to a certain time point. For example, when the certain time point is t, the time range may include t−50 seconds to t+300 seconds, and accordingly, the camera operating apparatus 100 may store all frames included in the images from t−50 seconds to t+300 seconds. In other words, the camera operating apparatus 100 may store every frame in the images within the time range from 50 seconds before the time point t to 300 seconds after the time point t, as the image of the time range corresponding to the time point t. The time range corresponding to a certain time point may be set by the user. As such, according to the present disclosure, when a certain event occurs, images before and after occurrence of the event are stored, and thus, the user may easily check a causal relationship of the event.

In addition, in the health-care mode of the camera operating apparatus 100, similar to the black-box mode described above, every frame included in images transmitted from the camera 500 within a time range corresponding to a certain time point is stored, and accordingly, bio-signals transmitted from the wearable sensor 310 may be stored after being mapped to the images. Accordingly, according to the present disclosure, a condition of the user 400 may be easily checked at each time point in an image.

The low-power mode of the camera operating apparatus 100 may be a mode, in which only some of a plurality of frames included in the images transmitted from the camera 500 are stored according to a frame selecting condition set in advance. Here, the frame selecting condition may be set by the user. The frame selecting condition may be for storing I frames, from an image including a plurality of I frames and a plurality of P frames. However, the present disclosure is not limited to the above example.

The camera 500 and the camera operating apparatus 100 may be set as one of various operating modes based on the bio-signals obtained by the wearable device 300, and operate in the above mode.

Figure 2:
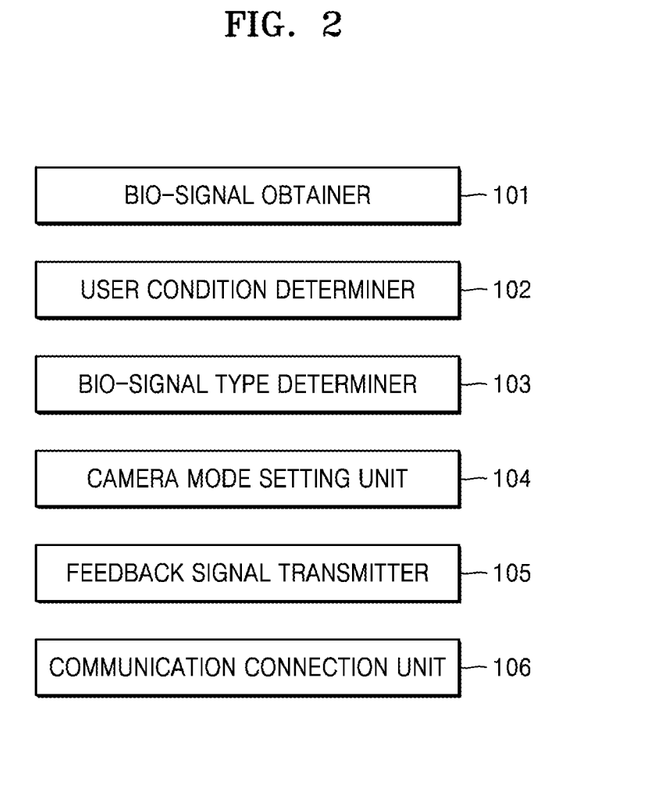
FIG. 2 is a block diagram of a camera operating apparatus based on bio-signals, according to an embodiment of the present disclosure.

FIG. 2 is a block diagram of a camera operating apparatus based on bio-signals, according to an embodiment of the present disclosure.

Referring to FIG. 2, the camera operating apparatus based on the bio-signals, according to an embodiment of the present disclosure, includes a bio-signal obtainer 101, a user condition determiner 102, a bio-signal type determiner 103, a camera mode setting unit 104, a feedback signal transmitter 105, and a communication connection unit 106.

The bio-signal obtainer 101, the user condition determiner 102, the bio-signal type determiner 103, the camera mode setting unit 104, the feedback signal transmitter 105, and the communication connection unit 106 may be computer programs stored in the program storage 130 (see FIG. 1) and executable by the controller 140 (see FIG. 1), sub-processors implemented in a processor corresponding to the controller 140 (see FIG. 1), or additional processors physically separated from the controller 140 (see FIG. 1).

That is, the controller 140 (see FIG. 1) executes or controls the bio-signal obtainer 101, the user condition determiner 102, the bio-signal type determiner 103, the camera mode setting unit 104, the feedback signal transmitter 105, and the communication connection unit 106 to provide various functions, such as obtaining a bio-signal, determining a type of the bio-signal, setting the mode of the camera, and generating a feedback signal.

In detail, the bio-signal obtainer 101 obtains a bio-signal of the user from the wearable sensor.

The bio-signal of the user may include an EEG measurement value, an EMG measurement value, a temperature measurement value, and an ECG measurement value.

For example, the bio-signal obtainer 101 may obtain the EEG measurement value obtained from the EEG sensor 311 (see FIG. 1), the EMG measurement value obtained from the EMG sensor 312 (see FIG. 1), the temperature measurement value obtained from the temperature sensor 313 (see FIG. 1), and the ECG measurement value obtained from the ECG sensor 314 (see FIG. 1) as bio-signals of the user.

The user condition determiner 102 determines whether the user is in a stable state, based on the bio-signals.

The user condition determiner 102 may determine whether the user is in the stable state by combining two or more bio-signals.

For example, the user condition determiner 102 may determine that the user is in the stable state, when a value measured by the ECG sensor is within a reference ECG range set in advance, or a value measured by the temperature sensor is within a reference temperature range set in advance.

Also, the user condition determiner 102 may determine that the user is not in the stable state when the value measured by the ECG sensor exceeds the reference ECG range set in advance, or the value measured by the temperature sensor exceeds the reference temperature range set in advance.

The bio-signal type determiner 103 may determine a type of the bio-signal, in a case where it is determined that the user is not in the stable state.

For example, when the value measured by the ECG sensor rapidly falls to exceed a reference fall range set in advance and the value measured by the temperature sensor falls beyond the reference temperature range set in advance, the bio-signal type determiner 103 may determine that the type of the bio-signal corresponds to 'heart attack' or 'risk of cardiac arrest'.

Also, when a state in which the value measured by the ECG sensor exceeds the reference ECG range and exceeds a reference time period set in advance and the value measured by the temperature sensor is higher than the reference temperature range set in advance, the bio-signal type determiner 103 may determine that the type of the bio-signal corresponds to 'brisk walking' or 'running'.

Also, when the value measured by the ECG sensor increases a small amount and exceeds the reference ECG range set in advance and the value measured by the temperature sensor rises above the reference temperature range set in advance, the bio-signal type determiner 103 may determine that the type of the bio-signal corresponds to 'excitement and joy'.

Also, when the value measured by the ECG sensor is within the reference ECG range set in advance and the value measured by the temperature sensor is within the reference temperature range set in advance, the bio-signal type determiner 103 may determine that the type of the bio-signal corresponds to a 'relaxed state'.

Also, when the value measured by the ECG sensor decreases by a small amount and falls beyond the reference ECG range set in advance and the value measured by the temperature sensor falls below the reference temperature range set in advance, the bio-signal type determiner 103 may determine that the type of the bio-signal corresponds to a 'depressed state'.

The camera mode setting unit 104 sets the camera 500 (see FIG. 1) to the mode according to the type of the bio-signal.

For example, when the type of the bio-signal corresponds to 'heart attack' of 'risk of cardiac arrest', the camera mode setting unit 104 may set the camera to the real-time live mode.

Also, when the type of the bio-signal is 'brisk walking' or 'running', the camera mode setting unit 104 may set the camera to the action cam mode.

Also, when the type of the bio-signal corresponds to 'excitement and joy', the camera mode setting unit 104 may set the camera to the high-resolution imaging mode.

Also, when the type of the bio-signal corresponds to a 'relaxed state', the camera mode setting unit 104 may set the camera to the low-power mode.

Also, when the type of the bio-signal corresponds to a 'depressed state', the camera mode setting unit 104 may set the camera to the real-time live mode.

When the camera 500 (see FIG. 1) is set to each of the modes described above, the camera operating apparatus 100 may also be set to a mode corresponding to each mode of the camera 500 (see FIG. 1). Detailed descriptions thereof are described above, and are omitted hereinafter.

The feedback signal transmitter 105 transmits a feedback signal to the wearable sensor based on an operating result of the camera.

The communication connection unit 106 may establish a communication connection between the camera 500 and the camera operating apparatus 100. As described above, the camera 500 may be provided separately from the camera operating apparatus 100 and the wearable device 300, and in this case, wired or wireless communication connection may need to be established for transmitting and receiving data between the camera 500 and the camera operating apparatus 100.

In more detail, the communication connection unit 106 may perform initialization of a communication channel and setting for data transmission/reception, according to a method of communication between the camera 500 and the camera operating apparatus 100. The detailed configuration of establishing the communication between the camera 500 and the camera operating apparatus 100 by the communication connection unit 106 may vary depending on the method of communication therebetween, and thus, detailed descriptions thereof are omitted.

In addition, although not shown in FIG. 2, the camera operating apparatus based on the bio-signal, according to the embodiment of the present disclosure, may further include an additional operation execution unit for performing additional operations, in addition to the setting of the operating mode of the camera according to the type of the bio-signal.

For example, when the type of the bio-signal corresponds to 'heart attack' or 'risk of cardiac arrest', the additional operation execution unit may transmit an alarm message to the user and a designated control server and transfer real-time images and a location of the user to call paramedics. Also, first-aid treatment corresponding to the heart attack may be provided to the user as an audio signal.

Also, when the type of the bio-signal corresponds to 'excitement and joy', the additional operation execution unit may execute a sound recording function to obtain images and sound together.

Also, when the type of the bio-signal corresponds to a 'depressed state', the additional operation execution unit may transmit an alarm message, real-time images, and a location of the user to contact information of family or friends of the user, set in advance.

Figure 3:
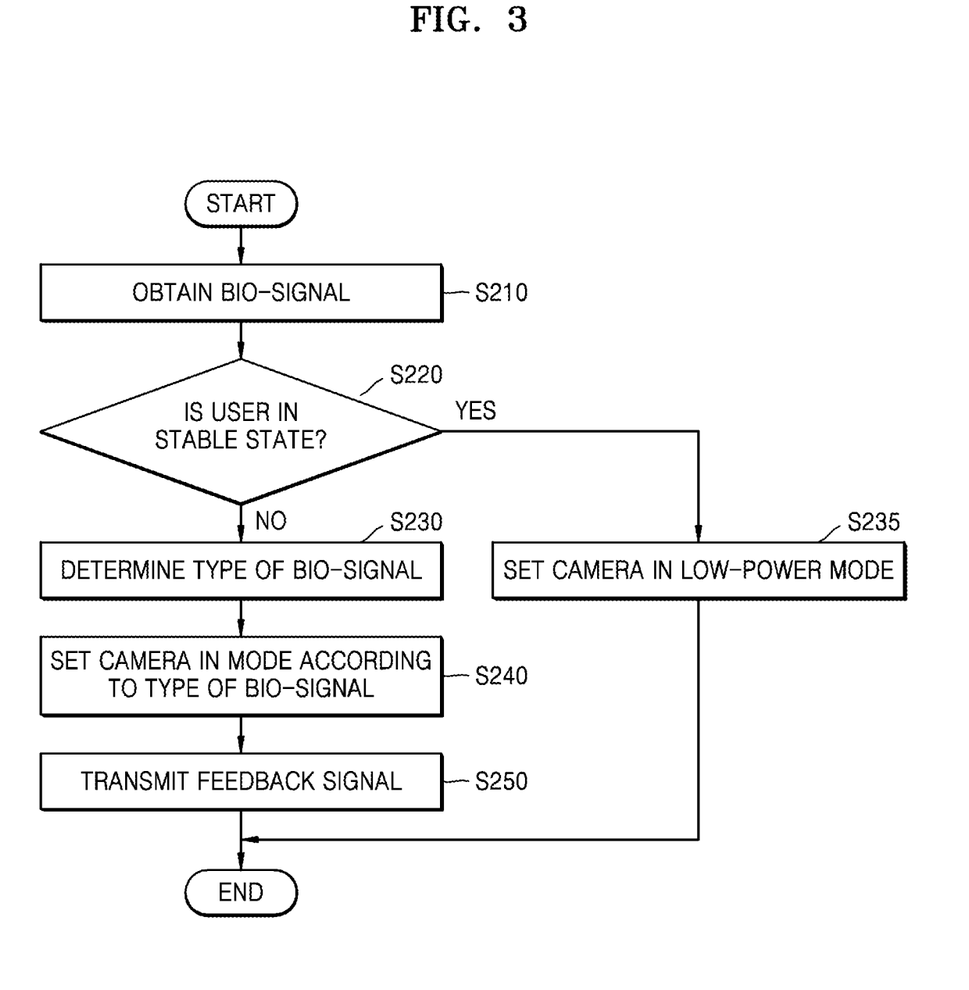
FIG. 3 is a flowchart illustrating a camera operating method based on bio-signals, according to an embodiment of the present disclosure.

FIG. 3 is a flowchart illustrating a camera operating method based on bio-signals, according to an embodiment of the present disclosure.

Referring to FIG. 3, the camera operating method based on bio-signals, according to the embodiment of the present disclosure, includes the bio-signal obtainer 101 obtaining bio-signals of the user from the wearable sensor (see FIG. 2) (S210).

Also, the camera operating method based on the bio-signals, according to the embodiment of the present disclosure, includes the user condition determiner 102 (see FIG. 2) determining whether the condition of the user is stabilized based on the bio-signal (S220).

Also, the camera operating method based on the bio-signals, according to the embodiment of the present disclosure, includes the bio-signal type determiner 103 (see FIG. 2) determining the type of the bio-signal when it is determined that the user is not in the stable state (S230).

Also, the camera operating method based on the bio-signals, according to the embodiment of the present disclosure, includes the camera mode setting unit 104 (see FIG. 2) setting the camera 500 (see FIG. 1) to a mode according to the type of the bio-signal (S240).

Also, the camera operating method based on the bio-signals, according to the embodiment of the present disclosure, may include the camera mode setting unit 104 (see FIG. 2) setting the camera to the low-power mode when it is determined that the user is in the stable state in S230 (S235).

Also, the camera operating method based on the bio-signals, according to the embodiment of the present disclosure, includes the feedback signal transmitter 105 (see FIG. 2) transferring a feedback signal to the wearable sensor based on the camera operation result (S250).

Figure 4:
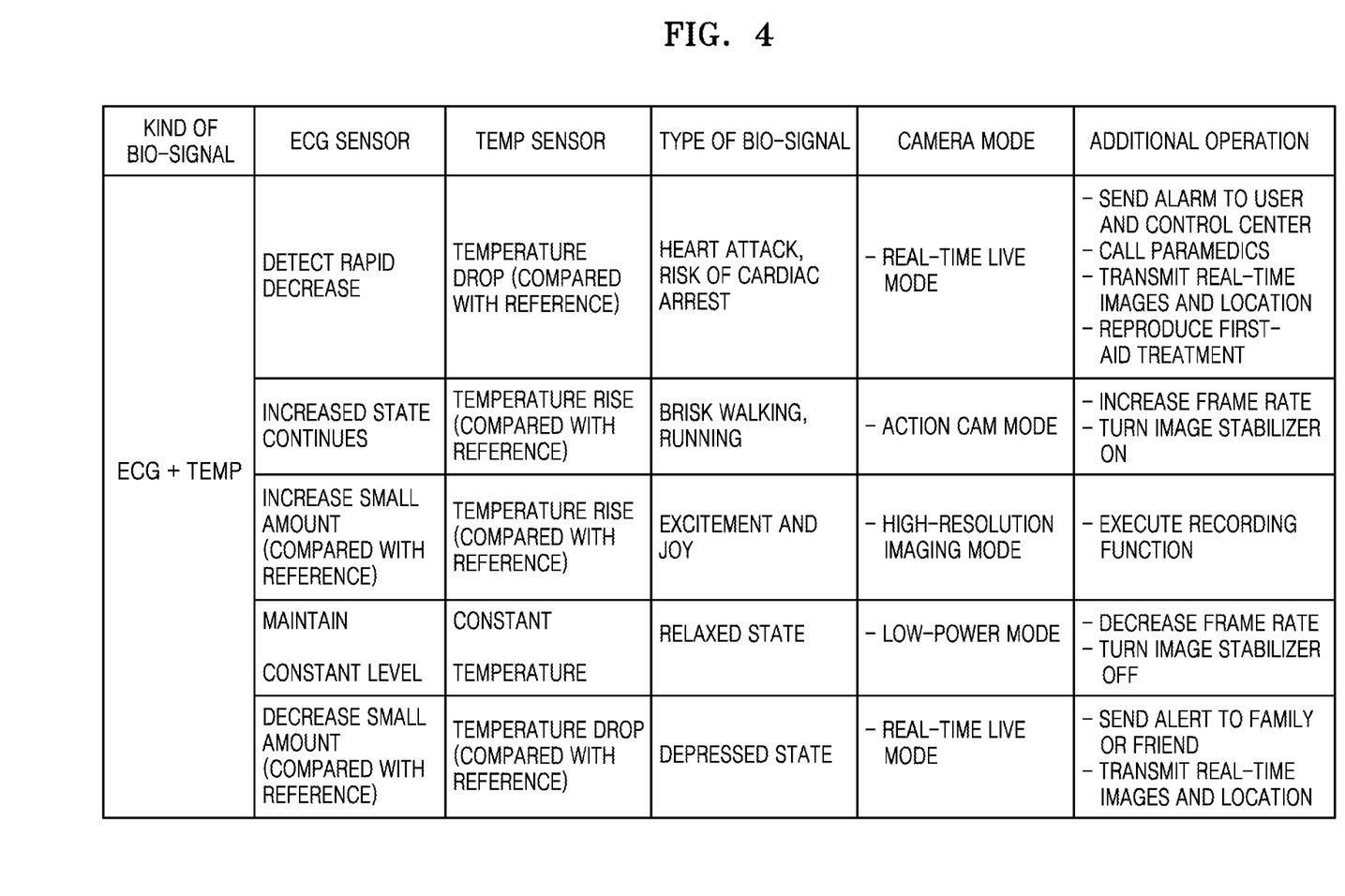
FIG. 4 is a diagram showing an example of determining a type of a bio-signal shown in FIG. 3.

FIG. 4 is a diagram showing an example of determining of a type of a bio-signal shown in FIG. 3.

Referring to FIG. 4, the bio-signal type determiner 103 (see FIG. 2) may determine the type of the bio-signal by combining two or more bio-signals.

For example, FIG. 4 shows an example, in which the bio-signal type determiner 103 (see FIG. 2) determines the type of the bio-signal by combining an EMG measurement value obtained from the EMG sensor 312 (see FIG. 1) and the temperature measurement value obtained from the temperature sensor 313 (see FIG. 1).

In detail, when the ECG value measured by the ECG sensor rapidly decreases lower than a reference ECG decrease range set in advance and the temperature value measured by the temperature sensor falls under a reference temperature range set in advance, the bio-signal type determiner 103 (see FIG. 2) may determine that the type of the bio-signal corresponds to 'heart attack' or 'risk of cardiac arrest'. In this case, the camera mode setting unit 104 (see FIG. 2) sets the camera to the real-time live mode, and the additional operation execution unit (not shown) transmits an alarm message to the user and a designated control server and transmits real-time images and a location of the user to the control server to call paramedics. Also, first-aid treatment corresponding to the heart attack may be provided to the user as an audio signal.

Also, when a state in which the value measured by the ECG sensor exceeds the reference ECG range and a reference time period set in advance and the value measured by the temperature sensor is higher than the reference temperature range set in advance, the bio-signal type determiner 103 (see FIG. 2) may determine that the type of the bio-signal corresponds to 'brisk walking' or 'running'. In this case, the camera mode setting unit 104 (see FIG. 2) may set the camera to the action cam mode.

Also, when the value measured by the ECG sensor increases a small amount and exceeds the reference ECG range set in advance and the value measured by the temperature sensor rises above the reference temperature range set in advance, the bio-signal type determiner 103 (see FIG. 2) may determine that the type of the bio-signal corresponds to 'excitement and joy'. In this case, the camera mode setting unit 104 (see FIG. 2) may set the camera to the high-resolution imaging mode, and the additional operation execution unit (not shown) may execute a sound recording function to obtain images and sound.

Also, when the value measured by the ECG sensor is within the reference ECG range set in advance and the value measured by the temperature sensor is within the reference temperature range set in advance, the bio-signal type determiner 103 (see FIG. 2) may determine that the type of the bio-signal corresponds to a 'relaxed state'. In this case, the camera mode setting unit 104 (see FIG. 2) may set the camera to the low-power mode.

Also, when the value measured by the ECG sensor decreases by a small amount and falls beyond the reference ECG range set in advance and the value measured by the temperature sensor falls below the reference temperature range set in advance, the bio-signal type determiner 103 (see FIG. 2) may determine that the type of the bio-signal corresponds to a 'depressed state'. In this case, the camera mode setting unit 104 (see FIG. 2) sets the camera to the real-time live mode, and the additional operation execution unit (not shown) may send an alarm message, real-time images, and a location of the user to contact information of family or friends of the user set in advance.

Figure 5:
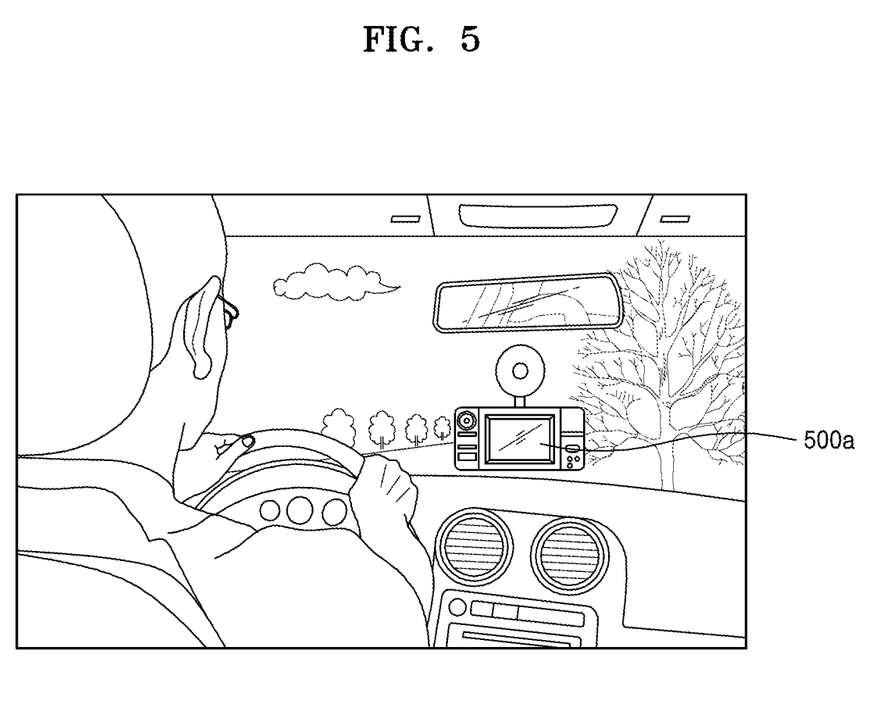
FIGS. 5 and 6 are diagrams illustrating an example in which a camera is provided in an external environment.
Figure 6:
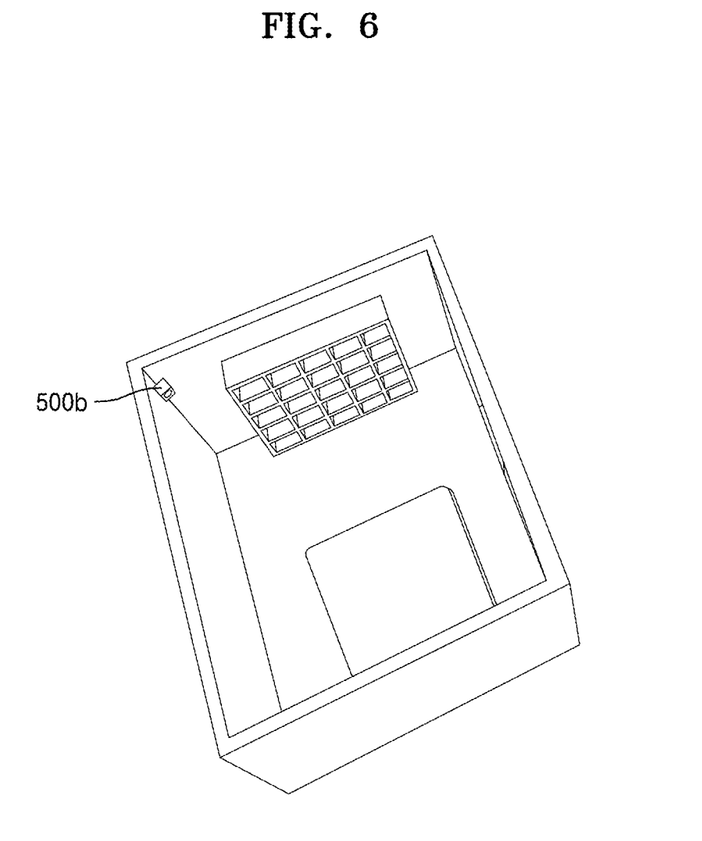

FIGS. 5 and 6 are diagrams illustrating an example in which the camera 500a or 500b is provided in an outer environment.

As described above, the camera 500a may be provided separately from the camera operating apparatus 100 and the wearable device 300. Here, the camera 500a may be an exclusive camera for capturing images according to the present disclosure, or may be a camera performing an independent function. For example, as shown in FIG. 5, the camera 500a may be a black-box installed in a vehicle. In other words, the black-box installed in the vehicle may perform as the camera 500a according to the present disclosure, in addition to functions of the black-box.

As shown in FIG. 5, when the black-box installed in a vehicle is the camera 500a, the camera operating apparatus 100 may set an operating mode of the black-box, that is, the camera 500a, according to the bio-signal of the user 400.

For example, when it is determined that the user 400 is in a nervous/excited state, the camera operating apparatus 100 may set the operating mode of the camera 500a as the high-resolution imaging mode and set the operating mode of the camera operating apparatus 100 as a black-box mode. Also, when it is determined that the user 400 is not in the nervous/excited state, the camera operating apparatus 100 may set operating modes of the camera 500a and the camera operating apparatus 100 as the low-power mode. Detailed descriptions of each mode are provided above, and thus are omitted hereinafter.

As such, according to the present disclosure, images suitable for each situation may be obtained by changing the operating mode of the camera 500a and/or the camera operating apparatus 100, and moreover, memory may be more efficiently used. Also, a camera that has already been provided in an external environment may be used, and thus, images may be obtained economically and efficiently.

As shown in FIG. 6, when CCTV installed in a house is a camera 500b, the camera operating apparatus 100 may set an operating mode of the camera 500b according to bio-signals of the user 400, and moreover, the camera operating apparatus 100 may store the bio-signals of the user 400 together with images captured by the camera 500b.

For example, when it is determined that the user 400 who is sleeping is in a state of a heart attack or risk of cardiac arrest, the camera operating apparatus 100 may set the operating mode of the camera 500b as the real-time live mode and the operating mode of the camera operating apparatus 100 as the health-care mode. When it is determined that the user 400 is not in the state of a heart attack, risk of cardiac arrest, or another emergency state, the camera operating apparatus 100 may set the operating modes of the camera 500b and the camera operating apparatus 100 as the low-power mode. Detailed descriptions of each mode are provided above, and thus are omitted hereinafter.

As such, according to the present disclosure, the operating mode of the camera 500b and/or the camera operating apparatus 100 may be changed according to the bio-signals of the user 400 so as to obtain images according to each situation, and moreover, a condition of the user 400 may be easily checked at each time point of the image.

Figure 7:
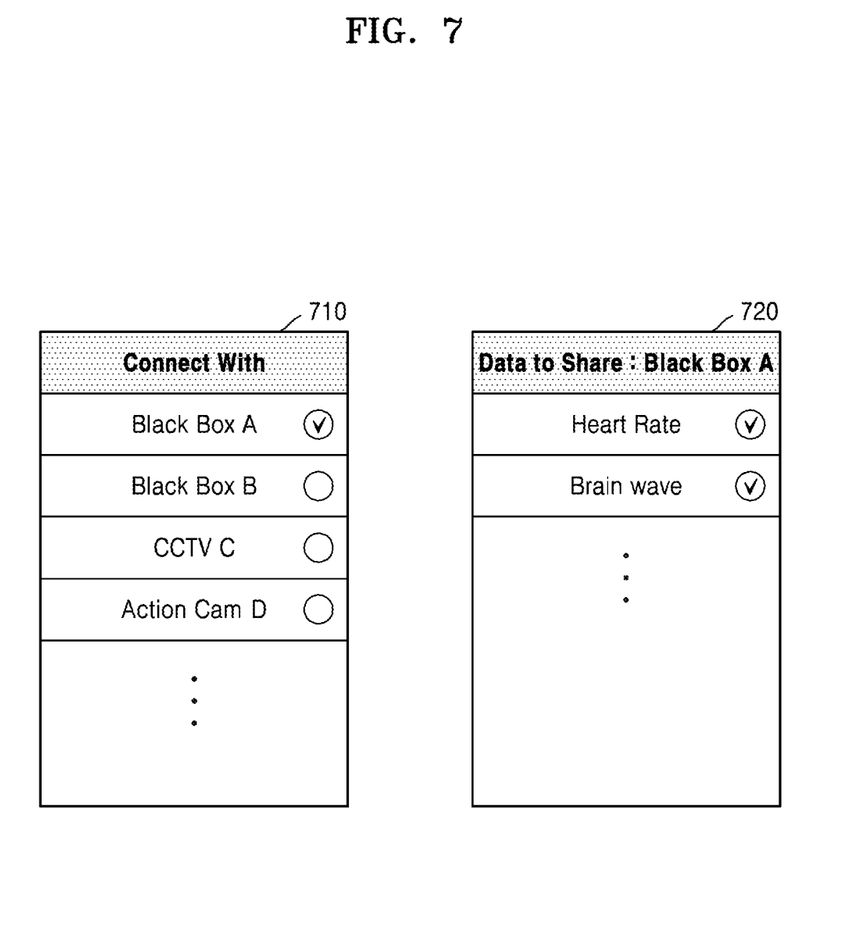
FIGS. 7 to 9 are diagrams illustrating a user interface according to an embodiment of the present disclosure.
Figure 8:
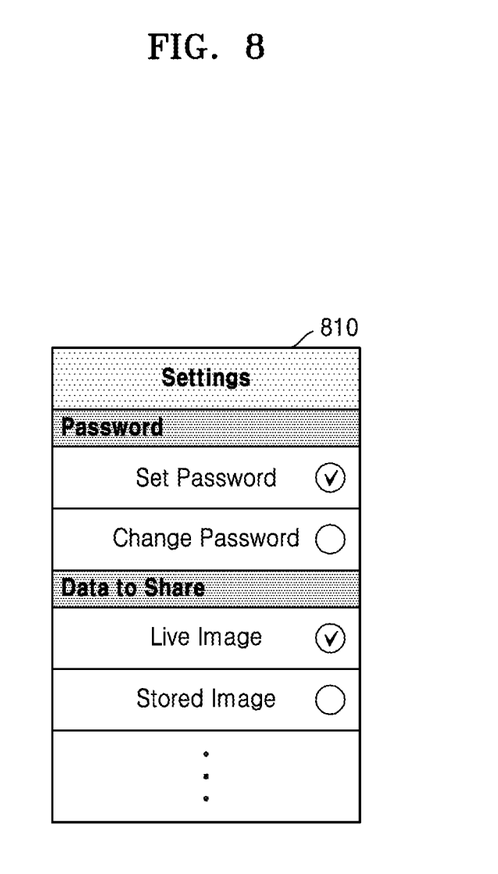
Figure 9:
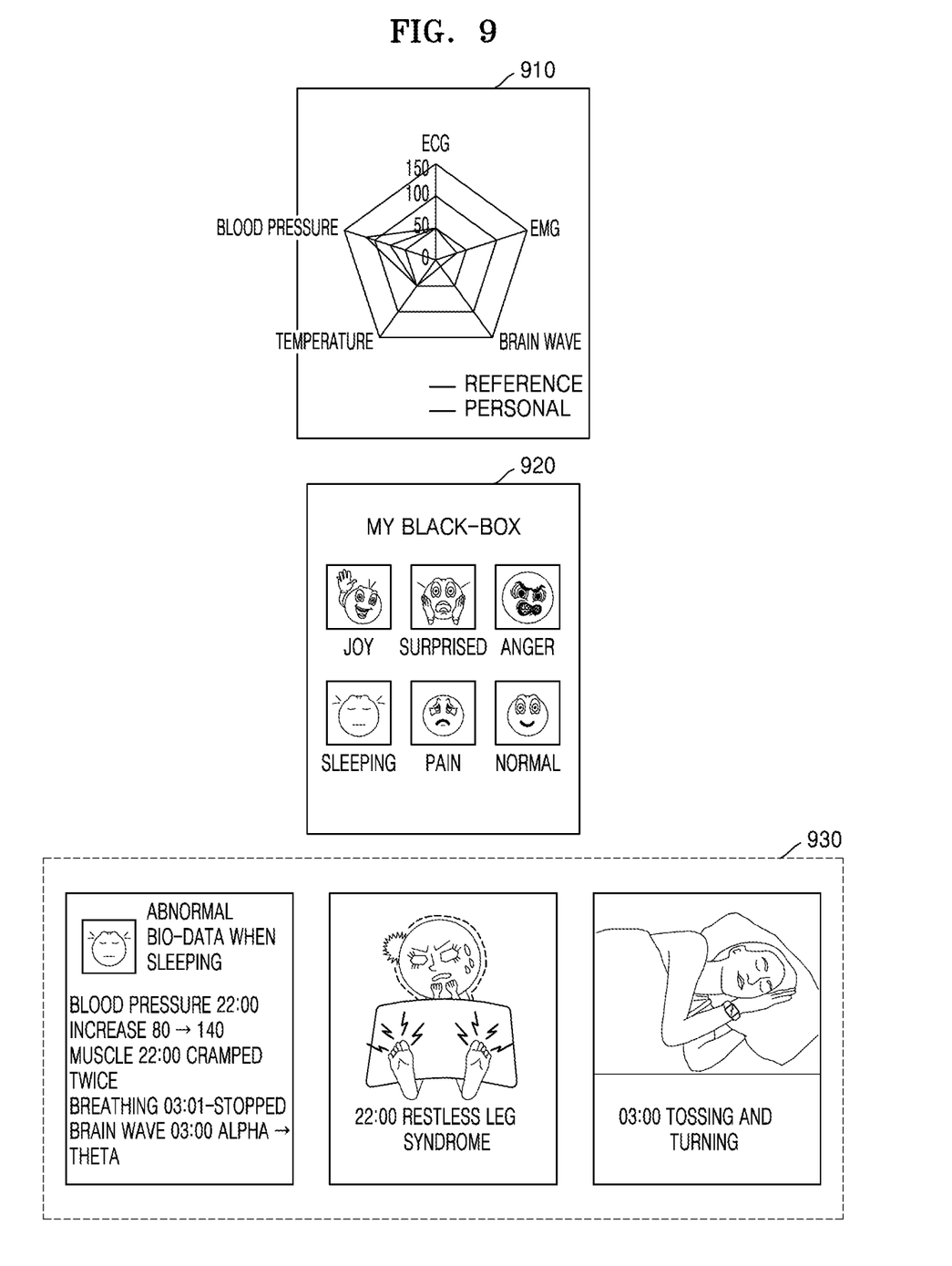

FIGS. 7 to 9 are diagrams illustrating a user interface according to an embodiment of the present disclosure.

FIG. 7 shows an example of a user interface for setting a connection between the wearable device 300 and the camera 500, the user interface being displayed on a display (not shown) of the camera operating apparatus 100.

Referring to a first screen 710, the user may set a connection target. As described above, the camera operating apparatus 100, the wearable device 300, and the camera 500 may be integrally provided, but also may be physically separate from one another. When the above components are physically separate from one another, the user may set communication connections among the components via the interface shown in FIG. 7.

For example, the user may select 'black-box A' from connection targets to connect the camera operating apparatus 100 to the camera 500, and in this case, the communication connection unit 106 may establish a communication connection between the camera operating apparatus 100 and the black-box A.

Referring to a second screen 720, the user may select an item to share with the connection target. For example, the user may share the items 'heart rate' and 'brain wave' with the 'black-box A'.

As described above, the user may establish the communication connections among the components via the interface shown in FIG. 7.

FIG. 8 shows an example, in which a user interface of the camera 500 for setting a connection to the camera operating apparatus 100 is displayed on the display (not shown).

Referring to a screen 810, the user may set a password to access the camera 500, or may set data of the camera 500 to be shared with the camera operating apparatus 100.

However, the screen 810 is an example, and when the camera 500 includes a display unit (not shown), the screen 810 may be displayed on the display unit of the camera, and when the camera 500 does not include a display unit, the screen 810 may be displayed on an external device (e.g., the camera operating apparatus) connected to the camera 500 via a network.

FIG. 9 shows an example of a screen of the camera operating apparatus 100 for displaying bio-signals transmitted from the wearable device 300.

Referring to a first screen 910, the camera operating apparatus 100 may display bio-signals in various ways. For example, as shown in the first screen 910, the camera operating apparatus 100 may display standard values and measured values of the ECG, EMG, brain wave, temperature, and blood pressure of the user 400 as figures, based on the bio-signals of the user 400 transmitted from the wearable device 300.

Referring to a second screen 920, the camera operating apparatus 100 may display condition information of the user based on the bio-signals. For example, the camera operating apparatus 100 may classify images obtained by the camera 500 into categories of 'joy', 'surprise', 'anger', 'sleeping', 'pain', and 'normal' based on the type of the bio-signals, and display each of the categories. Here, the user may select one of the categories and identify the images included in the selected category.

Also, the camera operating apparatus 100 may display summarized information of the bio-signals, as shown in a third screen 930. For example, the camera operating apparatus 100 may display times when main events occur, and may further display detailed content of an event when the user selects a time.

However, the interface and the screens provided above are examples, and the present disclosure is not limited thereto.

Information, layouts, etc. displayed on the screen may be determined according to setting by the user. At least one of the bio-signal, condition information of the user, and summarized information of the bio-signal may be displayed according to setting by the user.

The embodiment according to the present disclosure described above may be implemented in the form of a computer program that may be executed through a variety of components on a computer, and the computer program may be recorded in computer-readable media. Here, the media may include a hardware device that is specially configured to store and execute program instructions, for example, magnetic media such as a hard disk, a floppy disk, and magnetic tape media, optical recording media such as CD-ROM and DVD, magneto-optical media such as a floptical disk, and ROM, RAM, a flash memory, etc. Moreover, the media may include intangible media implemented in a transmittable form on a network, for example, media that may be implemented software or application forms to be transmitted and distributed through the network.

In addition, the computer program may be specially designed and constructed for the purposes, or may be of the kind well-known and available to those of skilled in the computer software arts. Examples of the computer program may include not only machine language codes made by a compiler, but also high-level language codes which are executable by various computing means by using an interpreter.

The particular implementations shown and described herein are illustrative examples of the present disclosure and are not intended to otherwise limit the scope of the present disclosure in any way. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical apparatus. Moreover, no item or component is essential to the practice of the present disclosure unless the element is specifically described as "essential" or "critical".

Therefore, the spirit of the present disclosure shall not be limited to the above-described embodiments, and the entire scope of the appended claims and their equivalents will fall within the scope and spirit of the disclosure.

The invention claimed is:

1. A method of operating a camera operating apparatus, the method comprising:
    obtaining a bio-signal of a user from a wearable sensor;
    determining, based on the bio-signal, whether the user is in a stable state;
    when the user is in the stable state, transmitting a first driving signal to a camera that is separately provided from the camera operating apparatus and the wearable sensor, to set the camera to a low-power mode so that the camera is enabled to capture an image the user in the low-power mode;
    when the user is not in the stable state, determining a type of the bio-signal, and transmitting a second driving signal to the camera to set the camera to a non-low-power mode according to the type of the bio-signal so that the camera is enabled to capture the image of the user in the non-low power mode.

2. The method of claim 1, wherein the determining of whether the user is in the stable state comprises, when a value measured by an electrocardiogram (ECG) sensor in the wearable sensor is within a reference ECG range set in advance and a value measured by a temperature sensor in the wearable sensor is within a reference temperature range set in advance, determining that the user is in stable state.

3. The method of claim 1, wherein the camera is provided in an external environment outside a wearable device comprising the wearable sensor.

4. The method of claim 3, further comprising setting a communication connection between the camera operating apparatus and the camera.

5. The method of claim 1,
    wherein the transmitting the second driving signal to the camera comprises
        transmitting the first driving signal to set the camera to one of the non-low-power mode comprising a real-time live mode in which the camera transmits the image of the user to the camera operating apparatus in real time, an action cam mode in which a frame rate of the camera is set to be greater than or equal to a reference frame rate and an image stabilizing function is turned on, and a high-resolution imaging mode in which the frame rate of the camera is set to be greater than or equal to a reference resolution,
    wherein the method further comprises storing every frame included in images transmitted from the camera, within a time range corresponding to a time point when it is determined that the user is not in the stable state and when the camera is set to the one of the non-low-power mode.

6. The method of claim 5, further comprising storing every frame after mapping the bio-signal to each frame, within the time range corresponding to the time point when it is determined that the user is not in the stable state.

7. The method of claim 1, further comprising, when the camera is set to the low-power mode, storing, according to a frame selecting condition set in advance, only some of a plurality of frames included in images transmitted from the camera.

8. The method of claim 1, further comprising transmitting a feedback signal to the wearable sensor, based on an operation result of the camera.

9. A method of operating a camera operating apparatus, the method comprising:
    obtaining a bio-signal of a user from a wearable sensor;

determining, based on the bio-signal, whether the user is in a stable state;

when the user is in the stable state, setting a camera to a low-power mode;

when the user is not in the stable state, determining a type of the bio-signal; and setting the camera to a mode according to the type of the bio-signal, wherein the setting of the low-power mode comprises setting a frame rate of the camera to be equal to or less than a reference frame rate set in advance, and turning off an image stabilizing function of the camera.

10. The method of claim 9, wherein the camera is a wearable camera provided on a body of the user.

11. A camera operating apparatus comprising:

a communication interface configured to obtain a bio-signal of a user from a wearable sensor; and at least one processor configured to implement:

a user condition determiner configured to determine, based on the bio-signal, whether the user is in a stable state;

a bio-signal type determiner configured to determine a type of the bio-signal, when the user is not in the stable state; and a camera mode setting unit configured to control the communication interface to transmit a first driving signal to a camera, that is provided separately from the camera operating apparatus and the wearable sensor, to set the camera to a low-power mode when the user is in the stable state so that the camera is enabled to capture an image of the user in the low-power mode, and control the communication interface to transmit a second driving signal to the camera to set the camera to a non-low-power mode according to the type of the bio-signal when the user is not in the stable state so that the camera is enabled to capture the image of the user in the non-low power mode.

12. The camera operating apparatus of claim 11, wherein the wearable sensor comprises an electroencephalography (EEG) sensor, an electromyography (EMG) sensor, an electrocardiogram (ECG) sensor, and a temperature sensor.

13. The camera operating apparatus of claim 11, further comprising a feedback signal transmitter configured to transmit a feedback signal to the wearable sensor based on an operating result of the camera.

14. The camera operating apparatus of claim 11, wherein the camera is provided in an external environment outside a wearable device comprising the wearable sensor.

15. The camera operating apparatus of claim 11, wherein the communication interface is further configured to establish a communication connection between the camera operating apparatus and the camera.

16. A camera operating system comprising:

at least one wearable sensor comprising at least one of an electroencephalography (EEG) sensor, an electromyography (EMG) sensor, an electrocardiogram (ECG) sensor, and a temperature sensor to obtain a bio-signal of a user;

a camera provided separately from the camera operating system and the at least one wearable sensor, and configured to capture images of the user; and at least one processor configured to obtain the bio-signal, to determine a condition of the user based on the bio-signal, and to transmit a driving signal to the camera to set a power mode of the camera based on the condition of the user.

* * * * *